United States Patent [19]

Aime et al.

[11] Patent Number: 5,368,839
[45] Date of Patent: Nov. 29, 1994

[54] INSOLUBLE SALTS OF LANTHANIDES FOR THE VISUAL DISPLAY USING NUCLEAR MAGNETIC RESONANCE, OF THE GASTRO-INTESTINAL TRACT

[75] Inventors: Silvio Aime; Mauro Botta, both of Milan, Italy

[73] Assignee: Bracco S.p.A., Milan, Italy

[21] Appl. No.: 941,069

[22] PCT Filed: Apr. 9, 1991

[86] PCT No.: PCT/EP91/00679
§ 371 Date: Nov. 6, 1992
§ 102(e) Date: Nov. 6, 1992

[87] PCT Pub. No.: WO91/16079
PCT Pub. Date: Oct. 31, 1991

[30] Foreign Application Priority Data

Apr. 12, 1990 [IT] Italy ............... 20026 A/90

[51] Int. Cl.$^5$ ............................................. A61B 5/055
[52] U.S. Cl. ......................................... 424/9; 436/173; 128/653.4; 424/617; 514/54; 514/57
[58] Field of Search ................. 424/9, 4, 5, 617; 436/173; 128/653.4, 654; 514/54, 57

[56] References Cited

U.S. PATENT DOCUMENTS

| | | | |
|---|---|---|---|
| 2,065,718 | 12/1936 | Menees et al. | 424/4 |
| 3,937,800 | 2/1976 | Dure-Smith et al. | 424/4 |
| 4,079,124 | 3/1978 | Winchell | 424/4 |
| 4,176,173 | 11/1979 | Winchell et al. | 424/5 |
| 4,615,879 | 10/1986 | Runge et al. | 424/9 |
| 4,735,796 | 4/1988 | Gordon | 424/9 |
| 5,043,101 | 8/1991 | Gordon | 252/408.1 |

*Primary Examiner*—Gary E. Hollinden
*Attorney, Agent, or Firm*—Buckman and Archer

[57] ABSTRACT

Diagnostic compositions particularly useful for NMR imaging of the gastrointestinal tract, comprise physiologically acceptable aqueous suspensions of insoluble salts of lanthanides, buffered, if required, at a pH value between 6.0 and 8.5 and which are, if required, formulated with appropriate insoluble organic or inorganic additives and/or with dispersing agents, suspending agents or viscosity-enhancing agents. These compositions are capable of increasing the value of the $r_2/r_1$ ratio, in which $r_1$ and $r_2$ are the longitudinal and transversal relaxivities of the protons of the surrounding water, thus permittting the production of clear images which have negative contrast and which lack artefacts of metallic type.

10 Claims, 1 Drawing Sheet

INSOLUBLE SALTS OF LANTHANIDES FOR THE VISUAL DISPLAY USING NUCLEAR MAGNETIC RESONANCE, OF THE GASTRO-INTESTINAL TRACT

The invention relates to suspensions of insoluble complexes or salts of lanthanide elements which are useful as contrast agents to produce NMR images of the gastrointestinal tract.

Currently, the techniques which are preferably employed for the diagnostic imaging of the abdomen include the use of X-rays, using suspensions of $BaSO_4$ as contrast agents, computerised axial tomography and ecography. However, nuclear magnetic resonance, although already capable of competing with axial tomography, especially as regards the assessment of focal lesions of liver, of tumors of suprarenal glands, of kidneys and of pelvic organs, has not yet reached an adequate level of application in the gastrointestinal field. This is due to the fact that the visual display of the gastroenteric tract presents numerous problems which are associated, inter alia, with intestinal motility, with anatomical variations in different patients, and with the fact that the irregularities of the intestinal loops may be confused with anomalous structures associated with pathological feature. Further, the observation of the principal abdominal organs, for example pancreas, is made difficult by the superposition of images from stomach and/or duodenum.

Accordingly, it is necessary to obtain a contrast agent which permits the application of a safe diagnostic technique such as NMR for the examination of these organs as well. Till now, studies have been carried out on various classes of substances: and initial classification may subdivide them into positive contrast agents, i.e. those which are capable of simultaneously reducing both the longitudinal relaxation time $T_1$ and the transverse relaxation time $T_2$ of the protons of the surrounding water, and negative contrast agents which act selectively on $T_2$. Actually, while the positive contrast agents permit improved observations of the organs in which they accumulate, the negative contrast agents have the function of eliminating the signal from the regions which contain them, thus permitting the delimitation of the contours of said regions and the visual display of the adjacent organs. In order to find positive contrast agents useful for the gastrointestinal tract, studies have been carried out on substances such as iron salts [Young et al., Computerized Tomography 5 (1981) 543-547; Wesbey et al., Magnetic Resonance Imaging 3 (1985) 57-64 and Radiology 149 (1983) 175-180; Clanton et al., Radiology 153 (1984) 159], gadolinium complexes [Weinmann et al., Radiology 153 ( 1984 ) 292 ]and chromium complexes [Kamisky et al., Magnetic Resonance in Medicine and Biology 1, (1988) 271]. On the other hand, with regard to negative contrast agents, consideration has been given to dispersions of diamagnetic substances such as kaolin or bentonite [Listinsky et al., Magnetic Resonance in Medicine 8 ( 1989 ) 285-92 ], while as far as their strong selective effect on $T_2$ is concerned, suspensions of appropriately supported ferromagnetic or superparamagnetic substances have been tested [Edelman et al., Radiology 161 (P) (1986) 314; Hahn et al., Radiology 164 (1987) 37-41]. Moreover, it is then necessary to consider those substances which cancel the NMR signal due to lack of protons, such as perfluoro derivatives [Mattrey et al., American Journal Roentgenology 148 (1987) 1259-1263 and Radiology 161 (P) (1986) 314].

Possible contrast agents for NMR imaging of the gastroenteric tract are described in Patent documents U.S. Pat. No. 4,719,098 (Gries), EP-A-275,215 (Amersham), U.S. Pat. No. 4,615,879 (Runge), EP-A-299,910 (Schering), WO 85/04330 (Nyegaard), WO 88/00060 (Adv. Magnetics) . Such agents may be classified as positive contrast agents, in the light of what has been described in U.S. Pat. No. 4,719,098, EP-A-275, 215, U.S. Pat. No. 4,615,879 and EP-A-299,911. On the other hand WO 85/04330 WO 88/00060WO85/05554 describe particles which act on the relaxation time T2, and are therefore potential negative contrast agents. The contrast agents for gastrointestinal use which have been studied up to the present time have not yet obtained the desired goals either as regards tolerability or as regards the possibility of obtaining images which are clear and which do not include artifacts of metallic type are due to a non-uniform distribution of the contrast agent in the tract to be examined.

It is known that parmagnetic metal ions, in particular those belonging to the transition metals or to the lanthanide elements, and their salts and/or complexes have the capacity to influence simultaneously and to a similar extent the relaxation times $T_1$ and $T_2$ of the protons of the surrounding water, thus behaving as positive contrast agents. The property is well documented, inter alia, in the above cited U.S. Pat. No. 4,615,879, in which a description is given of insoluble derivatives of gadolinium (especially gadolinium oxalate) for use in NMR diagnosis of the gastrointestinal tract.

It has now unexpectedly been found that certain salts and/or complexes of paramagnetic metal ions of the lanthanides group have the unexpected ability to selectively influence the relaxation time $T_2$ of the protons of the surrounding water, altering almost negligibly the time $T_1$ of the same. In this way, such compounds make it possible to increase the $r_2/r_1$ ratio, which corresponds to the ratio of the transverse and longitudinal relaxivities ($r_1$ and $r_2$ are inversely proportional to the relaxation times $T_1$ and $T_2$, see "Contrast and Contrast Agents in Magnetic Resonance Imaging" (1989) , P.A Rinck Ed., page 1, Recommendations for the Nomenclature of Magnetic Resonance Contrast Agent Terms). Therefore they are very promising negative contrast agents, particularly useful for the NMR examination of the gastrointestinal tract because they render it possible to obtain images clear and without those artefacts of metallic type which are caused, for example, by the selective $T_2$ contrast agents based on ferromagnetic or superparamagnetic substances such as magnetite and iron oxides. Such artefacts are generally caused by a local accumulation of the contrast agent, which generates a non-uniformity in the magnetic field, giving images which do not correspond to the actual pathological situation [see, in this connection, Lonnemark et al., Acta Radiologica 30 (1989) 193-196 and Bach-Gansmo et al,. "Contrast and Contrast Agents in Magnetic Resonance Imaging" (1989), P. A. Rinck Ed., pages 94-104 ].

It has been found that particularly suitable substances for the purpose of the invention are insoluble salts of lanthanides in which the metal ion is preferably selected from terbium, dysprosium, holmium, erbium and thulium and the anion is a suitable inorganic or organic insolubility-promoting anion which is physiologically compatible. Non-limiting examples of such anions may be selected from fluorides, oxalates and phosphates.

Substances which have proved to be particularly favourable within the scope of the present invention are the fluorides which combine a very low solubility, and thus a minimal absorption, with a marked selective reduction of the relaxation time $T_2$ of the protons of the surrounding water, thus permitting the achievement of high values of the ratio $r_2/r_1$.

The influence of the paramagnetic material on the $r_2/r_1$ ratio is also dependent upon the particle size of the particulate material: it has been found that generally a thinner particulate material is more effective in increasing the value of this ratio. For this purpose, it is possible to make use of particles having a diameter in the range between 0.01 and 1,000$\mu$ preferably between 0.05 and 500$\mu$.

The concentration of the insoluble paramagnetic particulate material may range between 0.01 and 5% (weight/volume) and preferably between 0.1 and 3%.

A further particularly significant aspect of the invention is also given by the completely unexpected finding that the addition of suitable insoluble particulate additives to the suspension of the salts and/or complexes of the lanthanides described above is capable of even further increasing the value of $r_2/r_1$, resulting in a further benefit for the purposes of NMR imaging. Such additives may be selected from organic or inorganic substances which are insoluble and physiologically compatible. As non-limiting examples from the point of view of a person skilled in the art, it is possible to mention cellulose derivatives such as hydroxymethylcellulose and carboxymethylcellulose among organic substances, and insoluble salts such as $BaSO_4$ or silica among inorganic substances.

In order to mantain the insolubility of the paramagnetic compounds of the invention during the passage in the district under examination, the suspensions of the same may be buffered at a suitable pH value using buffering agents which are physiologically compatible. Such a value is preferably neutral or slightly alkaline, i.e. in the range between 6.0 and 8.5.

In order to obtain satisfactory results from the diagnostic examination of the intestinal tract, it is also important that the contrast agent diffuse uniformly in the organ under examination and that the paramagnetic particulate material remain stable in suspension during the analysis, without giving rise to local accumulations. In order to achieve this objective, it is possible to use additives which are well known in the pharmacopoeia, like suspending agents, dispersing agents or viscosity-enhancing agents. If required, it is also possible to add excipients, edulcorating agents, flavourings, preservatives and additives in accordance with well known pharmaceutical formulation techniques.

The following examples serve to further illustrate the invention, without nevertheless limiting its applications, which are readily apparent to persons skilled in the art.

BRIEF DESCRIPTION OF THE DRAWINGS

Coronal section through the abdomen of a rat using nuclear magnetic resonance imaging after administration of a DyF3 suspension.

The products and reagents employed in the examples are commonly available commercially.

EXAMPLE 1

Figure 1:
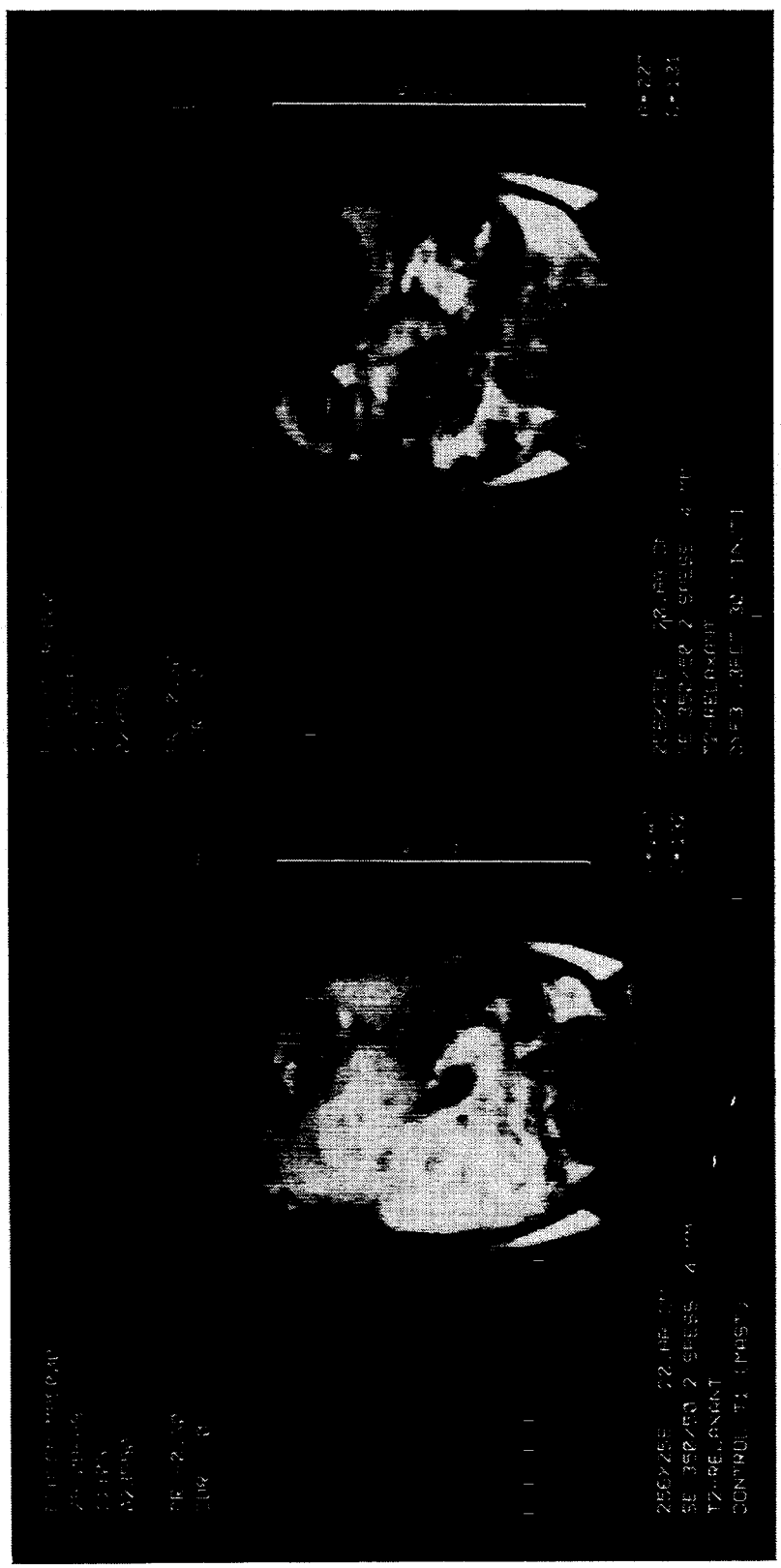

Preparation of insoluble salts of lanthanides: fluorides
Preparation of $HoF_3$

A few drops of concentrated HCl are added to a 250 ml beaker containing 100 ml of bidistilled water under magnetic agitation, to adjust the pH value between 1 and 2. 1.7 g of $HoCl_3.6H_2O$ (0.0045 mol) are then added. 0.74 g of NaF (0.0176 mol) is then added to the solution, and this is left under agitation for 30 minutes, maintaining the pH value between 1 and 2.

The precipitate is then filtered under vacuum, washed with 5 portions of 20 ml of bidistilled water, and dried at 100° C. for 4 hours. 0.98 g of $HoF_3$ is obtained (Yield: 98%).

The following salts are obtained using the same procedure:

| | |
|---|---|
| $GdF_3$ | (Yield: 98%) |
| $TbF_3$ | (Yield: 96%) |
| $DyF_3$ | (Yield: 99%) |
| $ErF_3$ | (Yield: 97%) |

EXAMPLE 2

Preparation of insoluble salts of lanthanides: oxalates
Preparation of $Dy_2(C_2O_4)_3$.

A few drops of dilute HCl (1:10) are added to a 250 ml beaker containing 100 ml of bidistilled water under magnetic agitation, to adjust the pH value between 3 and 4.

1.3 g of $DyCl_3.6H_2O$ (0.0034 mol) is then added.

0.6 g of oxalic acid (0.0067 mol) is added to the solution, and this is left under agitation for 40 minutes, maintaining the pH value between 3 and 4.

The precipitate is then filtered under vacuum, washed with 5 portions of 20 ml of bidistilled water, and dried at 100° C. for 4 hours.

0.97 g of $Dy_2(C_2O_4)_3$ is obtained (Yield: 97%).

The following are obtained using the same procedure:

| | |
|---|---|
| $Gd_2(C_2O_4)_3$ | (Yield: 98%) |
| $Tb_2(C_2O_4)_3$ | (Yield: 96%) |
| $Ho_2(C_2O_4)_3$ | (Yield: 96%) |
| $Er_2(C_2O_4)_3$ | (Yield: 97%) |

EXAMPLE 3

Preparation of suspensions of insoluble salts of lanthanides for the determination of the ratio $r_2/r_1$ Preparation of a 0.3% (weight/volume) $DyF_3$ suspension.

0.07 g of silicone SH and 0.3 g of $DyF_3$ are added, under agitation, to a 250 ml reactor equipped with a turbine-driven stirrer and containing 90 ml of distilled water.

After 5 minutes of stirring at ambient temperature, the following are added in order: 0.91 g of dibasic sodium phosphate, 0.2 g of monobasic potassium phosphate, 0.33 g of Keltrol F (Xanthan gum).

Stirring is continued for a further period of 10 minutes at such a speed as to prevent the inclusion of air. The volume is then made up to 100 ml with distilled water, and the agitation continues until complete homogenisation is achieved.

The dispersion obtained exhibits the following characteristics:

pH =7.3; viscosity=250 mPas.

0 3% (weight/volume) suspensions of the following salts are prepared following the same procedure:

| | | |
|---|---|---|
| HoF$_3$; | Dy$_2$(C$_2$O$_4$)$_3$; | DyPO$_4$ |
| GdF$_3$; | Ho$_2$(C$_2$O$_4$)$_3$; | HoPO$_4$ |
| TbF$_3$; | Gd$_2$(C$_2$O$_4$)$_3$; | GdPO$_4$ |
| ErF$_3$; | Tb$_2$(C$_2$O$_4$)$_3$; | ErPO$_4$ |

EXAMPLE 4

Determination of the ratio $r_2/r_1$ for the lanthanide salt suspensions of the present invention.

| - Experimental protocol | |
|---|---|
| A) Apparatus: | MINISPEC. PC 120 (BRUKER) |
| B) Observation frequency: | 20 MHz (proton) |
| C) Temperature: | 39° C., with previous thermostatic temperature control of the NMR sample ube for 10 minutes at working temperature. |
| D) Concentrations (weight/volume): | 0.01; 0.05; 0.25% |
| E) Samples: | Suspensions of the following salts (prepared in accordance with the procedure of Example 3): GdF$_3$, DyF$_3$, HoF$_3$, Gd$_2$(C$_2$O$_4$)$_3$, Dy$_2$(C$_2$O$_4$)$_3$, Ho$_2$(C$_2$O$_4$)$_3$, GdPO$_4$, DyPO$_4$, HoPO$_4$. |

The longitudinal relaxivity of the protons of the surrounding water ($r_1$) was calculated using the "Inversion Recovery" sequences in accordance with the program supplied for the MINISPEC 120 BRUKER with which the measurements were made.

The transverse relaxivity ($r_2$) was calculated using the Carr, Purcell, Meiboom and Gill sequences in accordance with the program supplied for the MINISPEC 120 BRUKER with which the measurements were made.

Table 1 attached hereto shows the efficacy (E) of certain lanthanide salts, of the present invention, in increasing the $r_2/r_1$ ratio. The efficacy (E) was calculated by adopting as reference term gadolinium fluoride (GdF$_3$) and was expressed as the ratio between the value of $r_2/r_1$ of the suspension of the lanthanide salt under examination and the corresponding value of $r_2/r_1$ found for the GdF$_3$ suspension. Table 1 shows the selective action on the reduction of the relaxation time $T_2$ of the protons of the surrounding water, with the consequent increase of the $r_2/r_1$ ratio, by the products object of the present invention with respect to the Gd salts adopted as reference terms.

EXAMPLE 5

Preparation of a DyF$_3$ suspension in the presence of carboxymethylcellulose.

A DyF$_3$ suspension is prepared in accordance with the procedure described in Example 3, using the following quantities:

| | |
|---|---|
| Bidistilled water | 90 ml |
| Silicone SH | 0.07 g |
| DyF$_3$ | 0.3 g |
| Na$_2$PO$_4$ | 0.91 g |
| KHPO$_4$ | 0.2 g |
| Keltrol F | 0.33 g |

Before making up to volume, are added 5 g of insoluble carboxymethylcellulose having a mean particle diameter of 10$\mu$, and agitation is maintained for 10 minutes.

The volume of the suspension is then brought to 100 ml using bidistilled water, and the agitation continues until complete homogenisation is achieved.

EXAMPLE 6

Determination of the ratio $r_2/r_1$ for the suspension described in Example 5.

In accordance with the experimental conditions described in the protocol of Example 4, the value of the ratio $r_2/r_1$ was measured for the DyF$_3$ suspension with the addition of carboxymethyl cellulose (DyF$_3$/CMC) and this was compared with that obtained for the suspensions of DyF$_3$ without carboxymethylcellulose (DyF$_3$) prepared as described in Example 3. The results, which are reproduced in Table 1 attached hereto, show a large increase, almost two-fold, in the value of this ratio for the suspension of DyF$_3$ with the addition of carboxymethylcellulose (DyF$_3$/CMC) with respect to that without such addition.

EXAMPLE 7

Preparation of a suspension of DyF$_3$ with the addition of BaSO$_4$.

98.64 g of BASO$_4$; 0.6 g of sorbitol and 0.1 g of silicone SH are added to a twin-cone mixer and mixed for 30 minutes. 0.3 g of sodium carragenate and 0.36 g of DyF$_3$ are then added in small portions.

After further mixing for 15 minutes, the mixture is poured into a 250 ml reactor and, under agitation, the volume is made up to 120 ml with distilled water.

EXAMPLE 8

Preparation of suspensions of insoluble salts of lanthanides of differing particle size.

Preparation of a DyF$_3$ suspension (325 mesh) 0.7 g of silicone SH and 3 g of DyF$_3$ (mean particle size 325 mesh) are added, under agitation, to a 500 m reactor equipped with a turbine-driven stirrer and containing 900 ml of distilled water. After 5 minutes stirring at ambient temperature, 8 g of Keltrol F (xanthan gum) are added in small portions.

After this, stirring is continued for a further period of 15 minutes at such a speed as to prevent the inclusion of air. The volume is then brought to 1000 ml using distilled water, and the agitation continues until complete homogenisation is achieved.

The dispersion obtained has a viscosity of 2000 mPas. 0.3% (weight/volume) suspensions of the following were prepared in accordance with the same procedure:

DyF$_3$ (particle size 60 mesh, mean diameter 250$\mu$)
TbF$_3$ (particle size 325 mesh, mean diameter 44$\mu$)
GdF$_3$ (particle size 325 mesh, mean diameter 44$\mu$)
HoF$_3$ (particle size 325 mesh, mean diameter 44$\mu$)

EXAMPLE 9

Determination of the $r_2/r_1$ ratio for the suspensions of insoluble salts of lanthanides of differing particle size.

The value of the $r_2/r_1$ ratio was measured for the suspensions of lanthanides described in Example 8, in accordance with the experimental conditions described in the protocol of Example 4.

Table 2 attached hereto shows the values of this ratio, from which it results that a thinner particle size is far more effective in increasing the value of $r_2/r_1$.

EXAMPLE 10

Acquisition of "in vivo" NMR images using a DyF$_3$ suspension according to the invention.

Experimental protocol.

The images were acquired on a 0.5 T "whole body imager" (Esaote-Genova), using a coil having an internal diameter of 8 cm.

In order to reduce the artefacts due to movement (respiration, peristalsis), use was made of a spin-echo sequence 350/50/2 (TR/TE/NEX) with a field of view of 20 cm, 4 mm slicers, 256×256 matrix, and with "gradient moment nulling".

A 3% (weight/volume) $DyF_3$ suspension, prepared in accordance with the preparation described in Example 3, was administered "per os" to (male) Sprague Dawley rats, average weight 270 g, which were kept under fasting conditions for 18 hours, at a dosage of 30 ml/kg.

The rat was observed using NMR for 1 hour after the administration. The contrast agent causes signal loss in the stomach and in the intestine. In the coronal sections observed at 30 minutes (FIG. 1 attached hereto), the stomach is clearly defined, permitting good observation of liver and spleen. The loop formed by the duodenum can also be observed.

tion and is capable of serving as a negative contrast agent and consisting of a physiologically acceptable aqueous suspension and administerable by the oral or rectal route, comprising insoluble particles of a paramagnetic material, said paramagnetic material being an insoluble salt of terbium, dysprosium, holmiun or erbium, and the insolubility-promoting anion being a fluoride, an oxalate or a phosphate ion.

2. The composition according to claim 1 which additionally contains at least one physiologically acceptable dispersing agent.

3. The composition according to claim 1 which contains at least one viscosity enhancing agent.

4. The composition according to claim 1 wherein said insoluble particles of said paramagnetic material have a mean dimension which ranges between 0.01 and 1,000$\mu$.

5. The composition according to claim 4 wherein said insoluble particles of said paramagnetic material have a mean dimension which ranges between 0.05 and 500$\mu$.

6. The composition according to claim 1 wherein said insoluble particles of said paramagnetic material are present in a concentration between 0.01% and 5% (weight/volume).

7. The composition according to claim 1 which additionally contains a buffering agent to maintain the pH between 6.0 and 8.5.

8. The composition according to claim 1 which further comprises at least one physiologically acceptable organic or inorganic insoluble additive.

9. The composition according to claim 8 wherein said physiologically acceptable insoluble organic additive is hydroxymethylcellulose or carboxymethylcellulose.

10. The composition according to claim 8 wherein said physiologically acceptable insoluble inorganic additive is $BaSO_4$ or silica.

TABLE 1

Efficacy (E) of the insoluble salts of lanthanides (LS) described in Examples 4 and 5 in increasing the $r_2/r_1$ ratio of the transverse and longitudinal relaxivities of the protons of the surrounding water.

| SL | $GdF_3$ | $DyF_3$ | $HoF_3$ | $Gd_2(C_2O_4)_3$ | $Dy_2(C_2O_4)_3$ | $Ho_2(C_2O_4)_3$ | $GdPO_4$ | $DyPO_4$ | $HoPO_4$ | $DyF_3/CMC**$ |
|---|---|---|---|---|---|---|---|---|---|---|
| E* | 1 | 25 | 20 | 0.5 | 4.7 | 4.8 | 0.2 | 2.4 | 3.8 | 45 |

*:The efficacy (E) is expressed by the ratio
$$\frac{r_2/r_1(SL)}{r_2/r_1(GdF_3)}$$

**:This is the suspension of $DyF_3$ with the addition of carboxymethylcellulose (CMC) described in Example 5

TABLE 2

Values of the $r_2/r_1$ ratio of the transverse and longitudinal relaxivities for the lanthanide salt suspensions described in Example 8.

|  | $GdF_3*$ | $TbF_3*$ | $DyF_3*$ | $DyF_3**$ | $HoF_3*$ |
|---|---|---|---|---|---|
| $r_2/r_1$ | 55 | 589 | 1037 | 147 | 764 |

*:Mean particle size 325 mesh (corresponding to a mean diameter of 44$\mu$.)
**:Mean particle size 60 mesh (corresponding to a mean diameter of 250$\mu$.)

We claim:

1. A composition for nuclear magnetic resonance imaging of the gastro-intestinal tract which is capable of increasing the value of the $r_2/r_1$ ratio of the relaxivities of the protons of the water of the region under examina-

* * * * *